(12) United States Patent
Seo et al.

(10) Patent No.: US 10,695,486 B2
(45) Date of Patent: Jun. 30, 2020

(54) LIQUID DRUG-FILTERING FILTER MEDIUM AND FILTER MODULE

(71) Applicant: AMOGREENTECH CO., LTD., Gyeonggi-do (KR)

(72) Inventors: In Yong Seo, Seoul (KR); Ui Young Jeong, Incheon (KR)

(73) Assignee: AMOGREENTECH CO., LTD., Gyeonggi-do (KR)

( * ) Notice: Subject to any disclaimer, the term of this patent is extended or adjusted under 35 U.S.C. 154(b) by 62 days.

(21) Appl. No.: 15/767,887

(22) PCT Filed: Oct. 14, 2016

(86) PCT No.: PCT/KR2016/011574
§ 371 (c)(1),
(2) Date: Apr. 12, 2018

(87) PCT Pub. No.: WO2017/065564
PCT Pub. Date: Apr. 20, 2017

(65) Prior Publication Data
US 2018/0304008 A1   Oct. 25, 2018

(30) Foreign Application Priority Data

Oct. 14, 2015 (KR) .................. 10-2015-0143649

(51) Int. Cl.
*A61M 5/165* (2006.01)
*A61M 5/178* (2006.01)
(Continued)

(52) U.S. Cl.
CPC ............ *A61M 5/165* (2013.01); *A61M 5/178* (2013.01); *A61M 5/3145* (2013.01);
(Continued)

(58) Field of Classification Search
None
See application file for complete search history.

(56) References Cited

U.S. PATENT DOCUMENTS

| 4,564,452 A | 1/1986 | Sharpe |
| 9,750,829 B2 * | 9/2017 | Kozlov ................ A61L 2/0017 |

(Continued)

FOREIGN PATENT DOCUMENTS

| CN | 202605880 | 12/1919 |
| CN | 102872729 | 1/2013 |

(Continued)

OTHER PUBLICATIONS

Widmark, Imaging-related medications: a class review, Proc (Bayl Univ Med Cent), 2007, 20(4):408-417 (Year: 2007).*

(Continued)

*Primary Examiner* — Chester T Barry
(74) *Attorney, Agent, or Firm* — Norton Rose Fulbright US LLP (57) ABSTRACT

A liquid drug-filtering filter medium is provided, which can include a nanofiber web having a three-dimensional network structure for filtering foreign substances included in a liquid drug. According to the embodiment, the occurrence of differential pressure when drawing in and filtering a liquid drug is minimized, and thus the liquid drug may be quickly drawn into a syringe cylinder within a short time and by applying small force, and at the same time, the filtration rate of foreign substances in the liquid drug is very outstanding. A method for producing the liquid drug-filtering filter medium is also provided, which enables the very easy adjustment of a pore structure of the filter medium or the diameters of the pores in order to enable the pore structure to minimize the occurrence of differential pressure or change the differential pressure to a target level.

13 Claims, 5 Drawing Sheets (51) Int. Cl.
*A61M 5/32* (2006.01)
*A61M 5/38* (2006.01)
*A61M 5/31* (2006.01)

(52) U.S. Cl.
CPC ............ *A61M 5/3297* (2013.01); *A61M 5/38* (2013.01); *A61M 2005/1655* (2013.01); *A61M 2205/75* (2013.01)

(56) References Cited

U.S. PATENT DOCUMENTS

| | | | |
|---|---|---|---|
| 2007/0075015 | A1 | 4/2007 | Bates et al. |
| 2008/0023394 | A1* | 1/2008 | Naruse ................ A61M 1/3679 210/483 |
| 2012/0117985 | A1* | 5/2012 | Urbahn .................. G01N 13/00 62/45.1 |
| 2013/0315817 | A1 | 11/2013 | Yamanoi et al. |
| 2015/0283032 | A1* | 10/2015 | Lin ....................... A61M 5/165 604/406 |
| 2018/0237315 | A1 | 8/2018 | Jeong |

FOREIGN PATENT DOCUMENTS

| | | |
|---|---|---|
| CN | 102947501 | 2/2013 |
| CN | 102958579 | 3/2013 |
| CN | 104785015 | 7/2015 |
| JP | 2003311263 | 11/2003 |
| JP | 2013022570 | 2/2013 |
| KR | 10-1675865 | 11/1916 |
| KR | 200233744 | 10/2001 |
| KR | 10-0887167 | 6/2003 |
| KR | 20140103866 | 8/2008 |
| KR | 10-0864063 | 10/2008 |
| KR | 10-0871440 | 12/2008 |
| KR | 10-2009-0128108 | 12/2009 |
| KR | 10-1452251 | 3/2010 |
| KR | 20110046907 | 5/2011 |
| KR | 10-2012-0002491 | 1/2012 |
| KR | 20130057973 | 6/2013 |
| KR | 20140025579 | 3/2014 |
| KR | 20140038157 | 3/2014 |
| KR | 20140137197 | 12/2014 |
| KR | 20140142018 | 12/2014 |
| WO | WO 2010011984 | 1/2010 |
| WO | WO 2011052865 | 5/2011 |

OTHER PUBLICATIONS

Office Action issued in Corresponding Korean Patent Application No. 10-2016-0133749, dated Jun. 17, 2019 (English Translation).
International Search Report and Written Opinion Issued in PCT Application No. PCT/KR2016/011574, dated Jan. 13, 2017.
International Search Report and Written Opinion Issued in Corresponding International Patent Application No. PCT/KR2016/008977, dated Jan. 6, 2017.
Office Action Issued in Corresponding Chinese Patent Application No. 201680047861.2, dated Aug. 28, 2019 (English Translation Provided).
Widmark, Jill M., "Imaging-related medications: a class review" *Baylor University Medical Center Proceedings 2007*, 20(4), 408-417.

* cited by examiner

LIQUID DRUG-FILTERING FILTER MEDIUM AND FILTER MODULE

CROSS-REFERENCE TO RELATED APPLICATIONS

This application is a national phase application under 35 U.S.C. § 371 of International Application No. PCT/KR2016/011574, filed Oct. 14, 2016, which claims priority to Korean Application No. 10-2015-0143649, filed Oct. 14, 2015. The contents of the referenced applications are incorporated into the present application by reference.

FIELD OF THE DISCLOSURE

The present invention relates to a liquid drug-filtering filter medium, and more specifically, to a liquid drug-filtering filter medium for filtering foreign matter such as glass powder which may be contained in a liquid drug before injecting the liquid drug into the human body through a syringe, a preparation method thereof, and a liquid drug-filtering filter module.

DESCRIPTION OF RELATED ART

For a medicinal liquid drug, a glass bottle is generally used as a storage container to prevent deterioration of the liquid drug. Further, it is common to produce a liquid drug in an ampoule container in which a glass bottle is filled with the liquid drug and sealed by melting an upper part of the glass bottle by heat to prevent foreign matter or various pathogens, viruses and the like contained in air from flowing into the glass bottle.

Further, the use of the liquid drug filled in the ampoule container is realized through a method in which the ampoule container is opened by cutting an upper part of the ampoule container, and then an injection needle is inserted through an opened space to draw the liquid drug into the cylinder. However, when the ampoule container is cut, glass fragments may flow into the ampule container and be mixed with the injection liquid. In this case, there is a problem that, when the liquid drug is injected into the human body, the glass fragments may also be injected.

In order to solve such a problem, a vial container in which the upper part of the glass bottle is sealed with a rubber stopper is used as a storage container for a liquid drug. The liquid drug stored in such a vial container is used by a method in which the injection needle directly passes through the rubber stopper and draws the injection liquid into the cylinder of the syringe.

However, when the injection needle is inserted into the vial container through the rubber stopper, there is a problem that the rubber debris infiltrates the injection needle or the inside of the vial container so that foreign matter may be mixed with the liquid drug and injected into the human body together with the liquid drug.

Since various types of diseases such as phlebitis and sepsis are caused when the glass fragments or rubber fragments are mixed with an injection liquid and injected into the body of the patient, a liquid drug filter for preventing the above-described problem has been studied. When developing liquid drug filters, a method of adjusting the pore diameter of the filter by performing a separate process such as biaxial stretching or the like on the prepared filter in order to filter particles with a fine particle size such as glass powder and the like is generally adopted. However, since the adjustment of the pore diameter of the filter using such a method controls a two-dimensional pore structure, there is a problem in that, when the liquid drug is drawn in by the syringe, the differential pressure is notably increased in the cylinder, and the flow amount of the liquid drug is significantly lowered. Considering that a nurse is generally a woman, the problem of significant differential pressure occurring in a syringe equipped with a conventional liquid drug filter is more serious. In the situation where a rapid response to emergency situations is required, the occurrence of the aforementioned problem interferes with timely medical treatment.

SUMMARY OF THE INVENTION

One object of the present invention is to provide a liquid drug-filtering filter medium, by which differential pressure generated when a liquid drug is drawn into a syringe through a filter medium is significantly reduced, and thus the liquid drug may be quickly drawn within a short time by applying a small force so that women may easily use the syringe, and the flow amount of liquid drug and the filtration efficiency of foreign matter in the liquid drug are notably increased, and a liquid drug-filtering filter module including the liquid drug-filtering filter medium.

Further, another object of the present invention is to provide a method of preparing a liquid drug-filtering filter medium, by which control of a pore structure and a pore diameter is very easy so that the occurrence of differential pressure is significantly reduced, and productivity may be enhanced.

Moreover, still another object of the present invention is to provide an injection device which includes the liquid drug-filtering filter module according to the present invention so that the occurrence of differential pressure is significantly reduced, and thus a liquid drug may be easily and quickly drawn into the syringe cylinder even by a weak woman.

In order to achieve the above-described objectives, the present invention provides a liquid drug-filtering filter medium including a nanofiber web having a three-dimensional network structure for filtering foreign matter included in a liquid drug.

According to one embodiment of the present invention, the nanofiber web may have a porosity of 40 to 90%, a basis weight of 1 to 10 g/m$^2$, a thickness of 1 to 20 μm and an average pore diameter of 0.3 to 3 μm.

Further, the nanofiber web may have an average diameter of 0.1 to 3 μm.

Further, the nanofiber web may include one or more selected from the group consisting of polyacrylonitrile (PAN), polyethersulfone (PES), thermoplastic polyurethane (TPU), polystyrene (PS) and a fluorinated compound, and the fluorinated compound includes one or more compounds selected from the group consisting of polytetrafluoroethylene (PTFE)-based, tetrafluoroethylene-perfluoroalkyl vinyl ether (PFA) copolymer-based, tetrafluoroethylene-hexafluoroprop ylene (FEP) copolymer-based, tetrafluoroethylene-hexafluoropropylene-perfluoroalkyl vinyl ether (EPE) copolymer-based, tetrafluoroethylene-ethylene (ETFE) copolymer-based, polychlorotrifluoroethylene (PCTFE)-based, chlorotrifluoroethylene-ethylene (ECTFE) copolymer-based and polyvinylidene fluoride (PVDF)-based compounds.

Further, the filter medium may further include a support disposed at one or both surfaces of the nanofiber web.

Further, the support may be one or more of a woven fabric, a knitted fabric or a nonwoven fabric.

Further, the support may include: a first support; and a second support disposed to surround side surfaces of the first support and having a melting point lower than that of a first support component forming the first support. Here, the first support component has a melting point of 180° C. or more, and the second support component has a melting point of 100 to 140° C.

Further, the nanofiber may have a nanofiber diameter uniformity of 25% or less according to the following Mathematical Equation 1.

[Mathematical Equation 1]

$$\text{Uniformity of nanofiber diameter (\%)} = \frac{\text{Standard deviation of nanofiber diameter (nm)}}{\text{Average diameter of nanofiber (nm)}} \times 100$$

Further, the nanofiber web may include a nanofiber including fiber-forming components including polyacrylonitrile (PAN) and polyvinylidene fluoride (PVDF) and an emulsifying agent for improving the miscibility of the fiber-forming components, and the fiber-forming components include polyacrylonitrile at 8 to 20 parts by weight based on 100 parts by weight of polyvinylidene fluoride, and the nanofiber includes an emulsifying agent at 0.5 to 8 parts by weight based on 100 parts by weight of the fiber-forming components.

Here, the emulsifying agent may be a nonionic emulsifying agent which improves spinnability, and the nonionic emulsifying agent may satisfy a hydrophile-lipophile balance (HLB) of 10 to 18.

Further, the present invention provides a method of manufacturing a liquid drug-filtering filter medium, including: (1) preparing a spinning solution including fiber-forming components and a solvent; and (2) electrospinning the spinning solution to produce a nanofiber web.

According to one embodiment of the present invention, Step (2) may include: 2-1) producing a nanofiber web by discharging the spinning solution on a support while applying air in the same direction as a discharging direction of the spinning solution adjacent to an outer periphery of a spinning nozzle; and 2-2) bonding the support and nanofiber web.

Further, in Step 2-2), the bonding may be performed by applying one or more of heat, ultrasonic waves, laser and high frequency waves to fuse the support and the nanofiber web, or the bonding may be performed by interposing an adhesive member between the support and the nanofiber web.

Further, the present invention provides a liquid drug-filtering filter module, including: the liquid drug-filtering filter medium according to the present invention; and a housing, including a liquid drug-inlet portion and a discharge portion through which a filtered liquid drug is discharged, and having the filter medium inside thereof.

Further, the present invention provides an injection device, including: the liquid drug-filtering filter module according to the present invention; and an injection module connected to a discharge portion of the liquid drug-filtering filter module.

According to the liquid drug-filtering filter medium of the present invention, the occurrence of differential pressure when drawing in and filtering a liquid drug is minimized, and thus the liquid drug may be quickly drawn into a syringe cylinder within a short time and by applying small force, and the filtration rate of foreign matter in the liquid drug is very outstanding. Further, a method for preparing the liquid drug-filtering filter medium according to the present invention enables the very easy adjustment of a pore structure of the filter medium or the diameters of the pores in order to enable the pore structure to minimize the occurrence of differential pressure or change the differential pressure to a target level, and at the same time, productivity is remarkably excellent, thereby enabling mass production and the wide application of the present invention across various industries such as the medical industry.

BRIEF DESCRIPTION OF THE DRAWINGS

FIGS. 1A and 1B is a cross-sectional view of a liquid drug-filtering filter medium according to one embodiment of the present invention.

DETAILED DESCRIPTION OF THE INVENTION

Hereinafter, embodiments will be described in detail with reference to the accompanying drawings so that those skilled in the art can easily carry out the embodiments. However, the embodiments may not be limited to those described below and may have various modifications. In addition, only components related to the embodiment are shown in drawings for the clarity of explanation and the same reference numerals will be assigned to the same or similar elements throughout the specification.

Figure 1A:
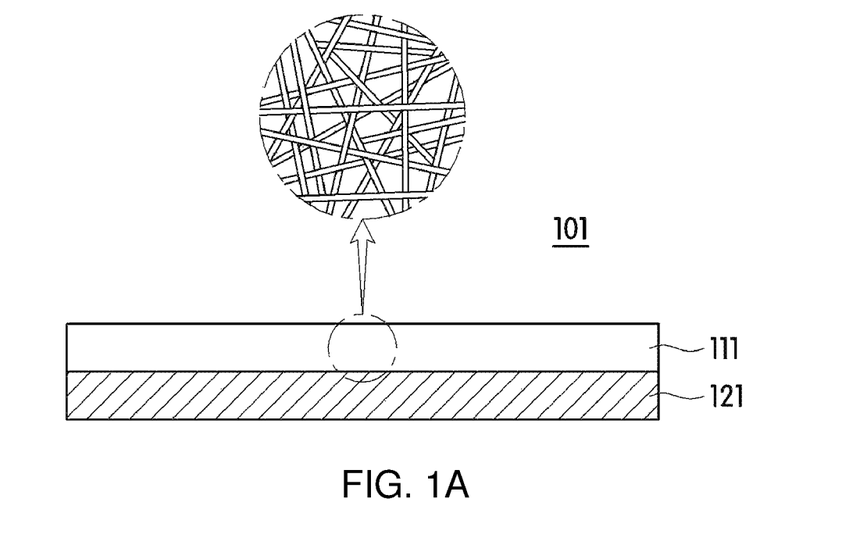
FIG. 1A is a view showing a filter medium in which a support is disposed at one surface of a nanofiber web.
Figure 1B:
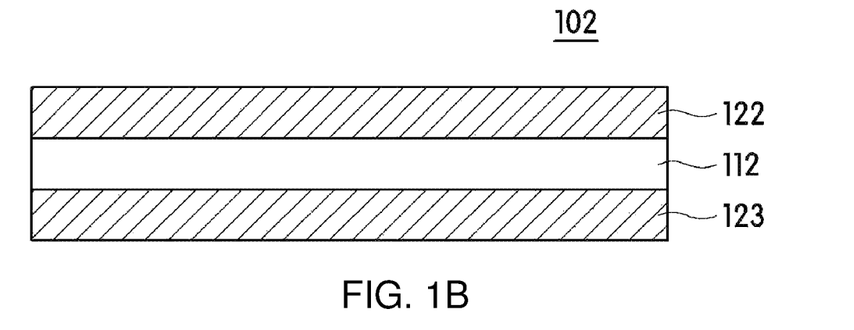
FIG. 1B is a view showing a filter medium in which supports are disposed at both surfaces of a nanofiber web.

As shown in FIGS. 1A and 1B, filter media for filtering a medicinal solution 101 and 102 according to one embodiment of the present invention may include nanofiber webs 111 and 112, and may further include supports 121, 122 and 123 at one or both surfaces of the nanofiber web 111 and 112.

Figure 2:
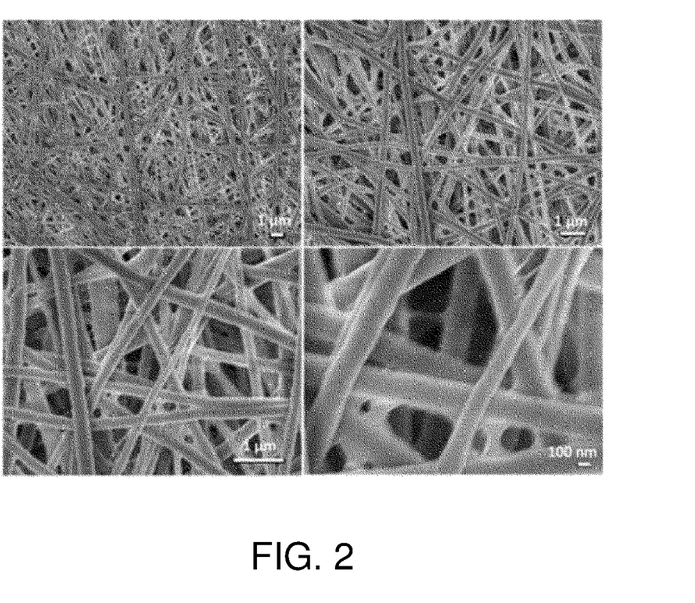
FIG. 2 is an SEM image of a nanofiber web included in one embodiment of the present invention.

The nanofiber webs 111 and 112 serve to filter a liquid drug, and have a three-dimensional network structure in which a plurality of strands of nanofibers are randomly and three-dimensionally stacked. Since the nanofiber web is formed of nanofibers, it may be more advantageous for implementing a fine pore size. Further, the nanofiber web has a three-dimensional network structure. Referring to FIG. 2, the nanofiber web may be formed by electrospinning.

Here, due to a remaining solvent which is not volatilized or evaporated in air during spinning, melt bonding (A) may occur at the portion in which fiber surfaces of the stacked nanofibers are in contact to form a three-dimensional network structure, and the structure may be more enhanced by primary calendering in a preparation method which will be described below. When a nanofiber web having a three-dimensional network structure is provided as a liquid drug-filtering filter medium, the generation of differential pressure during the drawing-in of the liquid drug is significantly reduced compared to a case in which a nanofiber web having a different shape or a different type is included, for example, the case in which a biaxially stretched filter medium is included, so that the flow amount of the liquid drug increases, and the liquid drug is more easily drawn into the cylinder.

Further, the nanofiber webs 111 and 112 included in one embodiment of the present invention have a thickness of 1 to 20 μm, and preferably 1 to 10 μm, a basis weight of 1 to 20 g/m², and preferably 1 to 10 g/m² based on a single layer. When a thickness of the nanofiber web is less than 1 μm and/or the basis weight is less than 1 g/m², mechanical strength is low so that it may be unsuitable to attain desired physical properties, for example, durability is lowered and the flow amount of the liquid drug is reduced. Further, when the thickness of the nanofiber web is more than 20 μm and/or the basis weight is more than 10 g/m², it may be difficult to attain desired physical properties, for example, the flow amount of the liquid drug and the occurrence of the differential pressure may increase.

Further, the nanofiber webs 111 and 112 may have a porosity of 40 to 90%. When the porosity is less than 40%, the occurrence of differential pressure increases while the liquid drug passes through the filter medium so that it may be difficult to easily draw the liquid drug into the syringe, and when the diameter of the syringe cylinder is small, drawing-in of the liquid drug may be more difficult due to the occurrence of differential pressure. Further, when the porosity is more than 90%, mechanical strength of the filter medium is low so that an initially designed three-dimensional network structure collapses when the filter medium is manufactured, distributed and/or mounted in the filter module and the filter module is used, and thus it may be difficult to attain desired physical properties, and for example, foreign matter may not be filtered at a desired level.

Further, the average pore diameter of the nanofiber webs 111 and 112 may be in the range of 0.3 to 3 μm. When the average pore diameter is less than 0.3 μm, differential pressure significantly occurs so that it may not be suitable for drawing the liquid drug into a cylinder having a small diameter such as a syringe. When the average pore diameter is more than 3 μm, filtration efficiency of glass fragments and the like may be remarkably lowered.

Further, the diameter of the nanofiber forming the nanofiber webs 111 and 112 may be in the range of 0.1 to 3 μm, preferably in the range of 0.2 to 1.5 μm, and more preferably in the range of 0.2 to 1 μm. Further, an aspect ratio may be in the range of 1000 to 100000, but is not limited thereto.

Further, the nanofiber diameter uniformity according to the following Mathematical Equation 1 may be 25% or less, preferably 18% or less, and more preferably 10% or less so that the pore size distribution of the filter medium is very uniform to increase filtration efficiency, and the differential pressure generated in the filter medium during filtration is significantly reduced.

[Mathematical Equation 1]

$$\text{Uniformity of nanofiber diameter (\%)} = \frac{\text{Standard deviation of nanofiber diameter (nm)}}{\text{Average diameter of nanofiber (nm)}} \times 100$$

Nanofiber diameter uniformity is a parameter which may be used to estimate the diameter distribution of the nanofibers forming the nanofiber web. A nanofiber diameter uniformity of 0% indicates that the standard deviation with respect to the diameter of the nanofiber is zero, that is, the nanofiber web is formed of nanofibers having the same diameter, and thus also indicates that the diameter uniformity is very high. When the nanofiber diameter uniformity is more than 25%, it may be undesirable for attaining desired physical properties, and for example, it may be difficult to achieve the flow amount, the filtration efficiency, and a decrease in generation of differential pressure at the same time.

Further, as a fiber forming component forming the nanofiber webs 111 and 112, any fiber forming component which is suitable for a conventional method of preparing the nanofiber such as electrospinning may be used without limitation. As non-limiting examples thereof, the fiber forming components may include polyethylene glycol derivatives including polyethylene glycol dialkyl ethers and polyethylene glycol dialkyl esters, polyoxides including poly(oxymethylene-oligo-oxyethylene), polyethylene oxide and polypropylene oxide, polyvinyl acetate, poly(vinylpyrrolidone-vinyl acetate), polystyrene and polystyrene acrylonitrile copolymers, polyacrylonitrile (PAN), polyacrylonitrile copolymers including polyacrylonitrile methyl methacrylate copolymers, polymethylmethacrylate, polymethylmethacrylate copolymers, fluorine-based compounds, polyethersulfone (PES), thermoplastic polyurethane (TPU), polystyrene (PS), or mixtures thereof.

Further, the fluorine-based compound may include one or more compounds selected from the group consisting of polytetrafluoroethylene (PTFE)-based, tetrafluoroethylene-perfluoroalkyl vinyl ether (PFA) copolymer-based, tetrafluoroethylene-hexafluoropropylene (FEP) copolymer-based, tetrafluoroethylene-hexafluoropropylene-perfluoroalkyl vinyl ether copolymer (EPE)-based, tetrafluoroethylene-ethylene (ETFE) copolymer-based, polychlorotrifluoroethylene (PCTFE)-based, chlorotrifluoroethylene-ethylene (ECTFE) copolymer-based and polyvinylidene fluoride (PVDF)-based compounds.

As an example, the nanofiber webs 111 and 112 may be nanofiber webs formed by only spinning PVDF to secure chemical resistance and heat resistance. Further, the surface of the nanofiber may be hydrophilized and modified by a hydrophilic polymer to improve the hydrophilicity of a PVDF nanofiber web. Specifically, in the case of the PVDF nanofiber web in which a hydrophilic polymer layer is formed, the hydrophilic polymer layer may be formed by including a hydrophilic polymer having a hydroxyl group, or may be formed by crosslinking of the hydrophilic polymer using a crosslinking agent. As an example, the hydrophilic polymer may be in the form of one or a mixture of polyvinyl alcohol (PVA), ethylenevinyl alcohol (EVOH), sodium alginate and the like, and most preferably, may be polyvinyl alcohol (PVA). Further, the crosslinking agent may be used without limitation as long as it is a known crosslinking agent having a functional group capable of crosslinking through a condensation reaction with a hydroxyl group possessed by the hydrophilic polymer. As an example, the functional group may be a hydroxyl group, a carboxyl group, etc. The hydrophilic polymer layer may be formed by crosslinking of polyvinyl alcohol (PVA) with a cross-linking agent including a carboxyl group to exhibit more improved physical properties. The polyvinyl alcohol may have a degree of polymerization of 500 to 2000, and a degree of saponification of 85 to 90%. When the degree of polymerization of the polyvinyl alcohol is excessively low, the formation of the hydrophilic polymer layer may not be smooth, or separation may easily occur even when the hydrophilic polymer layer is formed, and the degree of hydrophilicity may not be improved to a desired level. Further, when the degree of polymerization is too high, the hydrophilic polymer layer may be excessively formed so that the pore structure of the nanofiber web may change or pores may be clogged. Further, when the degree of saponification is too low, it may be difficult to improve hydrophilicity.

The cross linking agent may be a component containing a carboxyl group to be crosslinked with the polyvinyl alcohol described above. As an example, the crosslinking agent may include one or more materials selected from the group consisting of poly(acrylic acid-maleic acid), polyacrylic acid and poly(styrenesulfonic acid-maleic acid). Further, the cross-linking agent may be a polyfunctional cross linking agent having three or more carboxyl groups to be applied very thinly so that coating and adhesive properties on the hydrophobic surface of the nanofiber are more improved and the pore structure of the nanofiber web is not changed, and to exhibit more improved flux. When the crosslinking agent has less than three carboxyl groups, it is difficult to form a coating layer on the surface of the hydrophobic PVDF nanofiber, and even when the coating layer is formed, the adhesion force is very low so that the coating layer may be easily peeled off. As an example, the cross linking agent having three or more carboxyl groups may be poly (acrylic acid-maleic acid).

The hydrophilic polymer layer may be formed by crosslinking of 2 to 20 parts by weight of a cross-linking agent including a carboxyl group based on 100 parts by weight of the polyvinyl alcohol. When the cross linking agent is included at less than 2 parts by weight, the formability of the hydrophilic polymer layer may be reduced, and chemical resistance and mechanical strength may be lowered. Further, when the cross linking agent is included at more than 20 parts by weight, flux may be reduced because pores decrease due to the coating layer.

Further, the hydrophilic polymer layer may be formed on a part or all of the outer surfaces of the nanofibers forming the nanofiber web. Here, the nanofiber may be coated with the hydrophilic polymer layer so that 0.1 to 2 g of the hydrophilic polymer layer is included per unit area (m$^2$) of the fiber web.

The hydrophilic polymer layer may be formed by treating the PVDF nanofiber web with a hydrophilic polymer layer-forming composition. Here, the hydrophilic polymer layer may be formed by a method including treating the nanofiber web with the hydrophilic polymer layer-forming composition; and thermally treating the hydrophilic polymer layer-forming composition to form a hydrophilic polymer layer.

The hydrophilic polymer layer-forming composition may include a hydrophilic component and a cross-linkable component, for example, polyvinyl alcohol, a cross linking agent including a carboxyl group, and a solvent for dissolving the polyvinyl alcohol and the cross linking agent, such as water. The hydrophilic polymer layer-forming composition may include the cross linking agent at 2 to 20 parts by weight, and the solvent at 1,000 to 100,000 parts by weight based on 100 parts by weight of the polyvinyl alcohol.

Further, since the PVDF nanofiber web is highly hydrophobic, the coating layer may not be properly formed on the surface of the PVDF nanofiber web even when the surface is treated with the hydrophilic polymer layer-forming composition described above. Accordingly, the hydrophilic polymer layer-forming composition may further include a wettability enhancer so that the outer surface of the nanofiber is well wet.

As the wettability enhancer, any component may be used without limitation as long as it may improve the wettability of the outer surface of the hydrophobic PVDF nanofiber with a hydrophilic solution and may be dissolved in the hydrophilic polymer layer-forming composition. As an example, the wettability enhancer may be one or more components selected from the group consisting of isopropyl alcohol, ethyl alcohol and methyl alcohol. Further, the wettability enhancer may be included at 1,000 to 100,000 parts by weight based on 100 parts by weight of polyvinyl alcohol included in the hydrophilic polymer layer-forming composition. When the wettability enhancer is included at less than 1000 parts by weight, the improvement of the wettability of nanofibers is insignificant, and thus the formation of the hydrophilic polymer layer may not be smooth, and separation of the hydrophilic polymer layer may frequently occur. Further, when the wettability enhancer is included at more than 100,000 parts by weight, the degree of improvement of the wettability may be insignificant, and the concentration of the polyvinyl alcohol and the cross linking agent included in the hydrophilic polymer layer-forming composition is reduced so that the formation of the hydrophilic polymer layer may not be smooth.

Further, a hydrophilic polymer layer may be formed by pretreating the nanofiber web with a wettability enhancer and then treating the nanofiber web with a hydrophilic polymer layer-forming composition, without including the wettability enhancer in the hydrophilic polymer layer-forming composition. However, when the nanofiber web in which the wettability enhancer is supported in pores is immersed in the hydrophilic polymer layer-forming composition, the time required for the wettability enhancer which is supported in the pores to escape from the nanofiber web and for the hydrophilic polymer layer-forming composition to permeate the pores is long, and thus manufacturing time may be prolonged. Further, since the degree of penetration of the hydrophilic polymer layer-forming composition differs depending on the thickness and the pore diameter of the nanofiber web, a hydrophilic polymer layer may be formed non-uniformly according to the position of the fiber web. Furthermore, as the hydrophilic polymer layer is formed non-uniformly, the pores may be clogged by the hydrophilic polymer layer in a part of the nanofiber web, and in this case, the initially designed pore structure of the nanofiber web may be changed, and thus desired flux may not be obtained. Therefore, it is advantageous that the hydrophilic polymer layer-forming composition includes the wettability enhancer to shorten the manufacturing time, simplify the manufacturing process and improve the formability of the hydrophilic polymer layer without changing the pore structure of the nanofiber web.

Any known coating method may be used as a method of forming the hydrophilic polymer layer-forming composition on the nanofiber web without limitation, for example, immersion, spraying or the like may be used.

Thereafter, a step of forming a hydrophilic polymer layer by heat-treating the hydrophilic polymer layer-forming composition applied on the nanofiber web may be performed. Further, this step may be carried out simultaneously with a drying process of the solvent in the hydrophilic polymer layer-forming composition. The heat treatment may be performed in a drier, and the heat may be applied at a temperature of 80 to 160° C., and the heat treatment time may be 1 to 60 minutes, but the present invention is not limited thereto.

Further, as another embodiment for improving hydrophilicity, the nanofiber webs 111 and 112 may be a nanofiber web including PVDF and PAN. Here, PVDF and PAN may independently form nanofibers, and the independent nanofibers may be mixed to form a single web to prepare the nanofiber web. Alternatively, PVDF and PAN may be blended in the spinning solution and spun to prepare the nanofiber web including single nanofibers.

When PVDF and PAN are independently included in the spinning solution, there is no problem in spinnability, but when PVDF and PAN are mixed in the spinning solution and spun, spinnability may be lowered. According to one preferred embodiment of the present invention, the spinning solution may include fiber forming components including polyacrylonitrile (PAN) and polyvinylidene fluoride (PVDF) and an emulsifying agent for improving the miscibility of the fiber-forming components. The emulsifying agent serves to improve the miscibility of the fiber-forming components, and further improve the hydrophilicity of the nanofiber. Specifically, even when both of PVDF and PAN are dissolved in a specific solvent, the two components are not mixed uniformly in the solution due to having different properties, and even in a case of being mixed, the two components are only temporarily mixed by stirring or the like, and separation of the two components from the solution may easily occur over time. When such a solution is used as a spinning solution, the electrospun nanofiber is in a state in which the two components are not mixed, and specifically, the nanofiber having a structure in which, one component is spatially arranged like islands on the basis of another component, or one component is continuous and then another component is continuous, may be prepared, and thus the desired hydrophilicity and chemical resistance may not be uniformly exhibited at the same time. Further, since the nanofiber portion in which PAN is concentrated may be easily broken, mechanical strength is lowered, thereby significantly deteriorating the durability of the filter medium prepared therefrom.

Accordingly, it is necessary to mix two components having different properties so that the two components are evenly dispersed in the nanofiber. To this end, an emulsifier is necessarily included in the spinning solution. The emulsifying agent may include one or more selected from the group consisting of a cationic emulsifying agent, an anionic emulsifying agent, an amphoteric emulsifying agent and a nonionic emulsifying agent. However, the emulsifying agent may be a nonionic emulsifying agent for improving the spinnability and nanofiber diameter uniformity. When two or more types of emulsifying agents are mixed and used, one of the emulsifying agents is preferably a nonionic emulsifying agent. When a nonionic emulsifying agent is not included, for example, when an emulsifying agent is an ionic emulsifying agent, as electrical conductivity of a spinning solution is increased, the spinnability into fibers is notably decreased, and thus the solution is spun into beads or formed into a nanofiber including beads, causing low nanofiber diameter uniformity and non-uniform pore distribution in the fiber web layer.

The emulsifying agent may be selected from any known emulsifying agents, and is not particularly limited in the present invention.

Among the emulsifying agents, specific examples of the nonionic emulsifying agent that improves spinnability and uniformity include known nonionic emulsifying agents without limitation, and non-limiting examples thereof include an ethoxylate compound (e.g. alkylphenol polyethylene oxide condensate) synthesized by adding ethylene oxide to a hydrophobic compound such as a linear aliphatic hydrocarbon, an esterified product of a compound having a polyfunctional hydroxyl group or an adduct obtained by adding ethylene oxide to the esterified product, an adduct in which ethylene oxide is added to fatty acids, etc. Specifically, one or more of sugar alcohol fatty acid esters such as sorbitan fatty acid esters, polyoxyethylene sorbitan fatty acid esters and sucrose fatty acid esters, polyhydric alcohol fatty acid esters such as glycerin fatty acid esters, polyglycerin fatty acid esters, polyoxyethylene glycerin fatty acid esters, and polyethylene glycol fatty acid esters, ether type or ester type surfactants such as polyoxyethylene alkyl ethers, polyoxyethylene polyoxypropylene copolymers, polyoxyethylene alkyl phenyl ethers, and polyoxyethylene hydrogenated castor oil, and polyoxyethylene hydrogenated castor oil, fatty acid alkanolamides such as lauric acid diethanolamide may be used in combination as the nonionic emulsifying agent.

Further, a nonionic emulsifying agent included in the nanofiber according to one embodiment of the present invention may satisfy a hydrophile-lipophile balance (HLB) in the range of 10 to 18, and preferably in the range of 13 to 16. When a hydrophile-lipophile balance is less than 10, the degradation of miscibility of PVDF and PAN by the emulsifying agent may decrease the wettability of the nanofiber, and the diameter uniformity of spun nanofibers may be significantly lowered due to a decrease in miscibility and non-uniformity of solvent volatilization during spinning. Further, when the hydrophile-lipophile balance is more than 18, an emulsifying agent may be aggregately distributed during fiber formation, and may be susceptible to the influence of ambient temperature and humidity during spinning, solvent volatilization in a spinning solution may be non-uniform, and thus the diameter uniformity of the spun nanofibers may be significantly lowered. When one type of an emulsifying agent is included, a hydrophile-lipophile balance (HLB) of the emulsifying agent may be a hydrophile-lipophile balance of the corresponding component, and when two or more types of emulsifying agents are mixed, a hydrophile-lipophile balance (HLB) of the emulsifying agent may be a value of the hydrophile-lipophile balance finally calculated in consideration of the content and hydrophile-lipophile balance of each of the components.

Further, the nonionic emulsifying agent may be at 0.5 to 8 parts by weight based on 100 parts by weight of the fiber-forming components, and preferably at 1 to 5 parts by weight. When the nonionic emulsifying agent is included at less than 0.5 part by weight, phase separation of PVDF and PAN may occur before spinning, and accordingly the wettability of the fiber web may be non-uniform. Further, when the emulsifying agent is included at more than 8 parts by weight, the nanofiber is susceptible to the influence of ambient temperature and humidity during spinning, and solvent volatilization in a spinning solution may be non-uniform so that the diameter uniformity of the spun nanofibers may be significantly lowered, and thus it may be difficult to implement a fiber web having a desired pore size. In addition, a cationic emulsifier, an anionic emulsifier and/or an amphoteric emulsifier may be further included to improve the miscibility of PVDF and PAN, however, it is preferable to minimize the content thereof even when the above-described emulsifiers are included in terms of spinnability.

Next, the support layers 121, 122, and 123 are not particularly limited as long as the support layers generally serve as a support for a filter medium, but may preferably be a woven fabric, a knitted fabric or a nonwoven fabric in terms of the shape thereof. The woven fabric indicates that fibers included in the fabric have longitudinal and transverse directionalities, and the specific structure thereof may be a plain weave, a twilled weave and the like, and the density of warp and weft yarn is not particularly limited. Further, the knitted fabric may have a knit structure known in the related field, and may be a weave knitted fabric, a light knitted fabric and the like, but is not particularly limited thereto. Further, the nonwoven fabric may be a known nonwoven fabric such as a dry nonwoven fabric such as a chemical bonding nonwoven fabric, a thermal bonding nonwoven fabric, and an airlaid nonwoven fabric, a wet nonwoven fabric, a spunless nonwoven fabric, a needle punching nonwoven fabric, a meltblown nonwoven fabric. The pore diameter, porosity, basis weight and the like of the nonwoven fabric may vary depending on the desired permeability of the liquid drug, filtration efficiency, and mechanical strength, and thus are not limited in the present invention.

The support layers 121, 122, and 123 may be formed of any material without limitation, and non-limiting examples thereof include synthetic polymer components selected from the group consisting of polyester-, polyurethane-, polyolefin-, and polyamide-based components; or natural polymer components including cellulose-based components may be used. However, the material of the support layer preferably includes a known low-melting point component such as a known low-melting point polyester and a low-melting point polyethylene capable of thermal bonding in order to prevent separation of the support layer from the fiber web layer during the filtration process of the liquid drug by improving the binding force with the fiber web layers 111 and 112 described above, and to resolve a problem that the adhesive component is dissolved in the liquid drug and also injected into the human body due to the use of a separate adhesive component, and to allow the filter medium to be easily installed and fixed in the syringe or in the filter module. The low-melting point polymer compound may include a known low-melting point polymer compound having a melting point of 100 to 140° C. such as a low-melting point polyester, a low-melting point polyethylene, etc. As a specific example of the low-melting point polymer compound included in the support, a low-melting point fiber implemented using the low-melting point polymer as a fiber forming component may be included in the support, and the low-melting point fiber may be specifically a fiber in which the low-melting point polymer compound partially or entirely surrounds the outer portion of the core portion to perform a support function. The above-described fiber may be, for example, a polyester-based low-melting-point composite fiber having a low-melting-point polyester as a sheath portion and polyethylene terephthalate as a core portion and/or a polyolefin-based low-melting-point composite fiber having a low-melting point polyethylene as a sheath portion and a polypropylene as a core portion.

Figure 3:
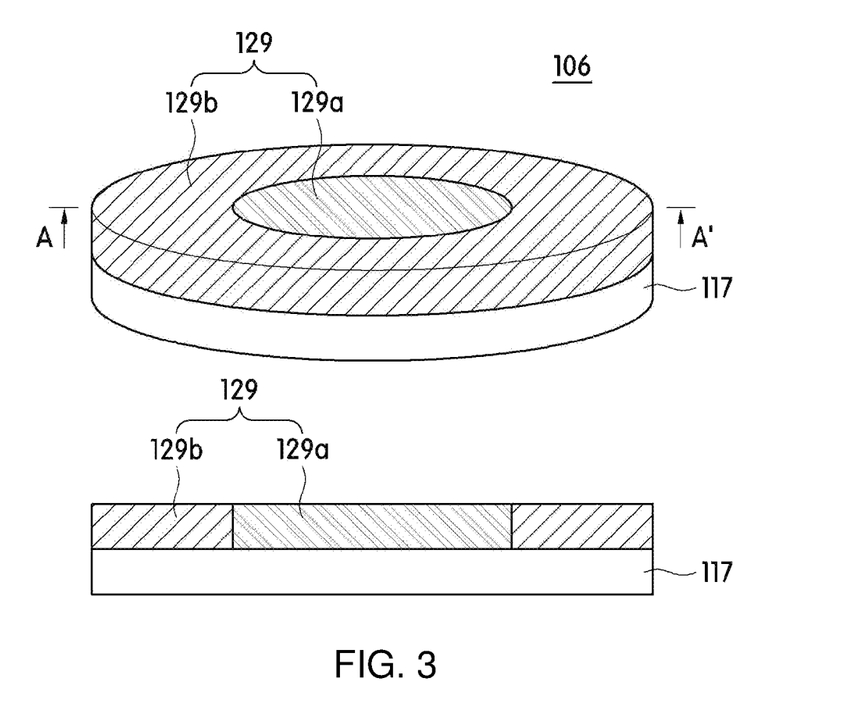
FIG. 3 shows a perspective view of a liquid drug-filtering filter medium according to one embodiment of the present invention, and a cross-sectional view taken along line A-A'.

Further, as shown in FIG. 3, the filter medium 106 may include a support 129 including two different type of supports 129*a* and 129*b*. Specifically, the support 129 may include a first support 129*a* and a second support 129*b* formed to surround the side surfaces of the first support 129*a*, and the second support 129*b* may be formed of a second support component having a melting point lower than that of the first support component forming the first support 129*a*.

That is, in the case where the support is implemented as a low-melting-point polymer compound as described above in order to adhere the support to the nanofiber web and/or adhere the filter medium to the inner wall of a housing which will be described below without using a separate adhesive agent, the mechanical strength of the support is low, and it may be difficult for the support to perform the original function as a support completely. In order to exhibit adhesion performance, the second support body 129*b* may include a low-melting point polymer compound to exhibit adhesion performance, and the first support 129*a* may be included together with the support 129 to complement the mechanical strength of the support 129 so that the support 129 exhibits both the supporting function and adhesive function at a desired level.

Further, since the second support 129*b* is disposed to surround the side surfaces of the first support 129*a* to implement the support 129 having a single layer to minimize an increase in thickness of the support 129, it is possible to prevent the differential pressure which may occur and/or increase due to an increase in the thickness of the nonwoven fabric, and it is advantageous for obtaining more improved flux. Further, the second support 129*b* disposed to surround the side surfaces of the first support 129*a* may allow the filter medium 106 to be more easily mounted and fixed to the inner surface of the housing in which the filter medium 106 is mounted by thermal bonding. Here, the first support component may have a melting point of 180° C. or more, and the second support component may have a melting point of 60 to 140° C., and may be preferably a polymer compound having a melting point of 100 to 140° C.

The filter media 101, 102 and 106 according to one example of the present invention as described above may be manufactured by a method including (1) preparing a spinning solution including fiber-forming components and a solvent; and (2) electrospinning the spinning solution to produce a nanofiber web. Accordingly, the three-dimensional network structure of the nanofiber web may be more easily formed, adjustment of the pore size of the nanofiber web becomes easy, and mass-production is possible, but the preparation method is not limited to the above-described method.

First, as Step (1) according to the present invention, a step of preparing a spinning solution including fiber forming components and a solvent is performed.

The type of the fiber forming component in Step (1) is the same as that described in the aforementioned material of the nanofiber, and thus the description thereof is omitted. The solvent may be used without limitation as long as the solvent does not cause precipitation while dissolving the fiber-forming components and does not affect the spinnability of the nanofiber which will be described below. Preferably, the spinning solution may include one or more selected from the group consisting of γ-butyrolactone, cyclohexanone, 3-hexanone, 3-heptanone, 3-octanone, N-methylpyrrolidone, dimethylacetamide, dimethyl sulfoxide and dimethylformamide.

The fiber forming components may be contained in the spinning solution at 5 to 30 wt %, and preferably at 8 to 20 wt %. When the fiber forming components are included at less than 5 wt %, it is difficult to form fibers, and the spinning solution is not spun into a fiber and spun in droplets to form a film phase, and even if spinning is performed, many beads are formed and the volatilization of solvent is not performed well, so that pores may be clogged in a calendering process which will be described below. Further, when the fiber-forming components are contained at more than 30 wt %, viscosity increases so that solidification occurs on the surface of the solution, and thus it is difficult to spin for a long time. Further, the fiber diameter may increase, and thus a fibrous phase with a sub-micrometer size may not be formed.

Next, as Step (2) according to the present invention, a step of producing a nanofiber web by electrospinning the spinning solution is performed.

Figure 4:
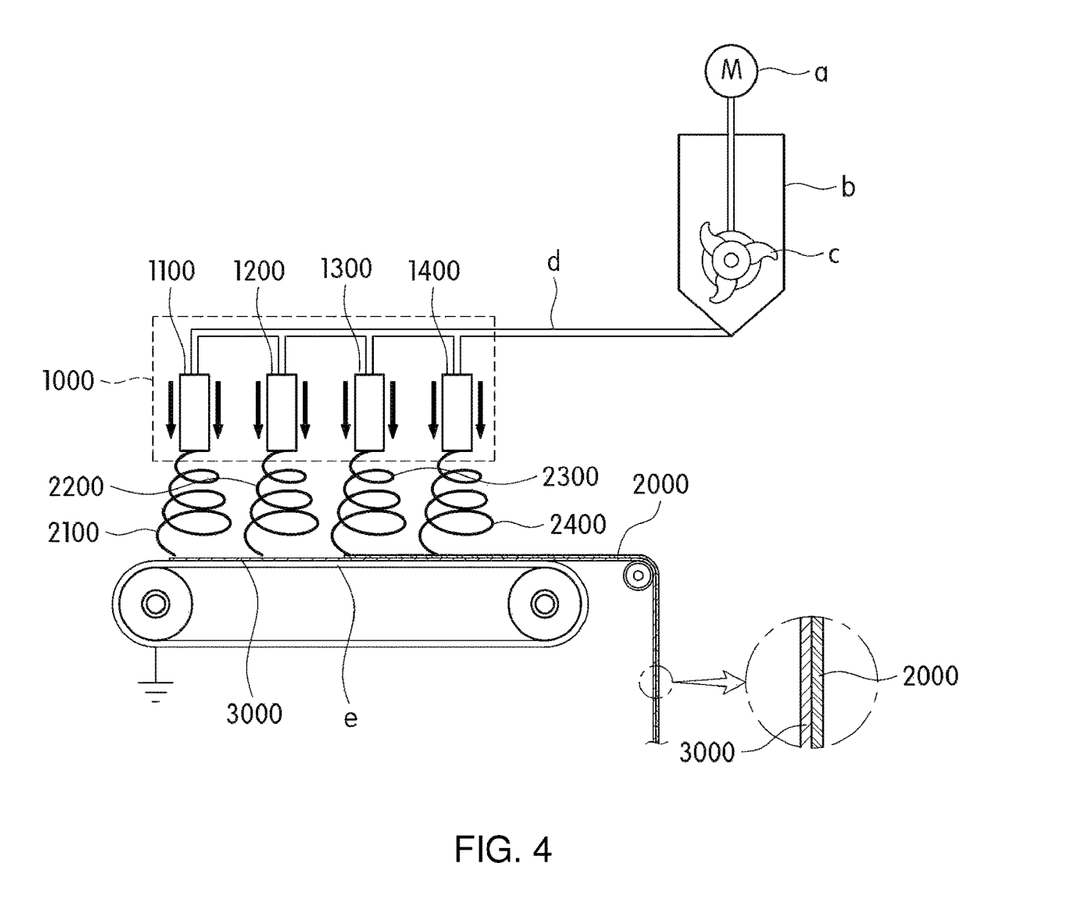
FIG. 4 is a schematic view of an electrospinning device capable of producing a filter medium according to an embodiment of the present invention through a continuous process.

Referring to FIG. 4, electrospinning may be performed by an electrospinning device including a solution tank (b), in which the spinning solution prepared in Step (1) is stored, and a spinning pack 1000 in which a plurality of spinning nozzles 1100, 1200, 1300 and 1400 connected to a high voltage generator (not shown) are arranged in a plurality of rows or columns. The spinning pack 1000 is disposed above a grounded collector (e) in the form of a conveyor moving at a predetermined speed, and a plurality of spinning nozzles are arranged at a predetermined distance so as to be orthogonal to the traveling direction of the collector (e). For convenience of explanation, FIG. 4 shows an electrospinning device in which four spinning nozzles are arranged at a predetermined distance along the traveling direction of the collector (e). The number of the spinning nozzles may be, for example, 30 to 60, or more as necessary. When a plurality of spinning nozzles are used as described above, the rotation speed of the collector (e) may be increased to improve productivity.

The solution tank (b) may contain a stirrer (c) using a mixing motor (a) as a driving source and may be connected to the spinning nozzles 1100, 1200, 1300 and 1400 of each row through a metering pump not shown in the drawing and a transfer tube (d). The spinning solution sequentially discharged from the spinning nozzles 1100, 1200, 1300 and 1400 of four rows is discharged as each of the nanofibers 2100 to 2400 while passing through the spinning nozzles 1100, 1200, 1300 and 1400 charged by a high voltage generator, and is sequentially accumulated on a grounded collector (e) in the form of a conveyor moving at a predetermined speed to form a fiber web 2000.

Further, Step (2) may include: 2-1) producing a nanofiber web by discharging the spinning solution on a support while applying air in the same direction as a discharging direction of the spinning solution adjacent to an outer periphery of a spinning nozzle; and 2-2) bonding the support and nanofiber web.

That is, when the spinning solution is simply discharged through the spinning nozzle and accumulated on the collector (e), the degree of accumulation of the prepared nanofiber web may be lowered, and breakage of fibers may frequently occur. That is, in the case of using the spinning pack 1000 having a plurality of spinning nozzles for mass production, mutual interference occurs between the spinning nozzles so that fibers are blown away and are not fully collected, and fibers may be collected while scattering. As a result, a nanofiber web thus obtained becomes too bulky, acting as a cause of spinning trouble. In order to solve this problem, air may be applied adjacent to the outer periphery of the spinning nozzle in the same direction as the discharging direction of the spinning solution. As air is applied to the nanofiber spun by the spinning nozzle in the same longitudinal direction as the fiber discharge direction while surrounding the outer periphery of the spun nanofibers, the volatility of the solvent in the spinning solution is increased, and this may help to solidify the fiber-forming components and collect and accumulate the spun nanofibers on the collector, thereby reducing spinning trouble, and help to obtain nanofibers with improved mechanical strength.

Further, a method of emitting the air applied to the spun nanofibers through an air nozzle disposed adjacent to the spinning nozzle through which the spinning solution is discharged, or a method of using a double-spinning nozzle as a spinning nozzle for discharging the spinning solution so that the spinning solution is discharged through a spinneret of a central portion and air is emitted through a spinneret surrounding the central portion, may be used. The latter method may be more suitable in terms of uniform contact of the nanofibers with air.

The air pressure of air emitted through the air jet nozzle disposed adjacent to each spinning nozzle of the spinning pack 1000 or the outermost spinneret of the double-spinning nozzle may be set as 0.01 to 0.2 MPa. When the air pressure is less than 0.01 MPa, it may not contribute to collection, accumulation and improvement of mechanical strength of the nanofibers. Further, when the air pressure of the emitted air is more than 0.2 MPa, the cone of the spinning nozzle is hardened to generate blocking of needles, causing spinning trouble, and the diameter uniformity of the prepared nanofibers may be significantly reduced.

Further, when the spinning process is performed by an air electrospinning (AES) method, the temperature and humidity inside a spinning chamber affects volatilization of a solvent from a spun fiber. When proper conditions are not set, the fiber is not properly formed or it is difficult to control the diameter of the fiber. Further, as beads are locally formed on the surface of the fiber, there is a problem that pores may be clogged in the pore control and heat treatment process of the fiber web which will be described below.

Further, it is preferable that the temperature and humidity inside the spinning chamber are set to be constant when the spinning solution is continuously and sequentially spun through four rows of spinning nozzles 1100, 1200, 1300 and 1400. When the temperature and humidity conditions inside the spinning chamber are different, either the spinning nozzle 1100 of the first row or the spinning nozzle 1200 of the second row may not spin, or the web produced according to the following process and the web produced according to the previous process may be separated due to decreased adhesion. The temperature of the spinning chamber is preferably set as 20 to 30° C., and the humidity thereof may be set as 20 to 50%.

Further, when the spinning solution is spun, the injection rate of the spinning solution per nozzle 1100, 1200, 1300 and 1400 may be in the range of 10 to 30 μl/min. Further, a distance between the tip of the nozzle and the collector may be in the range of 10 to 30 cm. However, the present invention is not limited thereto, and may be changed according to purpose.

As shown in FIG. 4, when the electrospun nanofibers 2100, 2200, 2300 and 2400 are collected on top of the collector as a conveyor belt type, a support 3000 capable of serving as a support for the filter media may be arranged on the collector, and the spun nanofibers 2100, 2200, 2300 and 2400 may be accumulated on the support 3000 to form the nanofiber web 2000 integrally formed with the support.

Thereafter, heat or pressure may be applied for control of the pore size and porosity of the nanofiber web 2000 formed on the support 3000, drying of the solvent and moisture remaining in the nanofibers, and improvement of mechanical strength of the nanofiber web. Here, the temperature of the applied heat may be in the range of 60 to 190° C., and the pressure may be in the range of 0.1 to 10 kgf/cm², but the present invention is not limited thereto. Further, the process of applying heat and/or pressure may be performed by a common calendering process, and the calendering process may be performed once or several times depending on the purpose.

Further, as Step 2-2) for bonding the prepared nanofiber web with the support, the support and the nanofiber web may be fused by applying at least one of heat, ultrasonic waves, laser, and high frequency waves, or an adhesive member may be interposed between the support and the nanofiber web to bond the support and the nanofiber web. The fusing may be performed by additionally applying separate heat and pressure after the calendering process, or may be performed simultaneously with the aforementioned calendering process. In the case of the bonding by ultrasonic waves, laser, and high frequency waves, since the frequency and intensity vary depending on the specific type of the fiber forming component of the nanofiber forming the nanofiber web and the material of the support, the detailed description thereof is omitted in the present invention, and each method may be performed by a known method.

Further, the filter media 101, 102, 104, 105, and 106 according to one embodiment of the present invention are mounted and fixed in a housing (not shown) including a liquid drug inlet and a discharge unit through which the filtered liquid drug is discharged to be implemented as a liquid drug-filtering filter module (not shown). The filter module may be provided inside the cylinder of the syringe, between the cylinder of the syringe and the injection cap, inside the injection cap and/or inside the needle, or may be connected outside the needle. As the cylinder, the injection cap and the like of the syringe, any cylinder and injection cap of a known syringe may be used without limitation. Further, the filter module according to one embodiment of the present invention may be implemented in an injection device by connecting an injection module such as a conventional syringe to a discharge portion provided in the filter module.

As an example thereof, an injection device having a liquid drug-filtering filter module mounted on an injection needle of the injection module will be described. Referring to FIGS. 5 to 8, the injection device according to one embodiment of the present invention includes: a cylinder 10 in which an injection liquid is stored; a plunger 12 installed in the cylinder 10 to be linearly movable and injecting or discharging an injection liquid into the cylinder 10; an injection module having an injection needle 20 mounted in front of the cylinder 10; and a liquid drug-filtering filter module 40 detachably mounted on the injection needle 20 to filter foreign matter such as glass fragments or rubber fragments when the injection liquid stored in an ampule glass bottle or a vial container is injected into the cylinder 10 so that only the pure injection liquid is stored in the cylinder 10.

Figure 5:
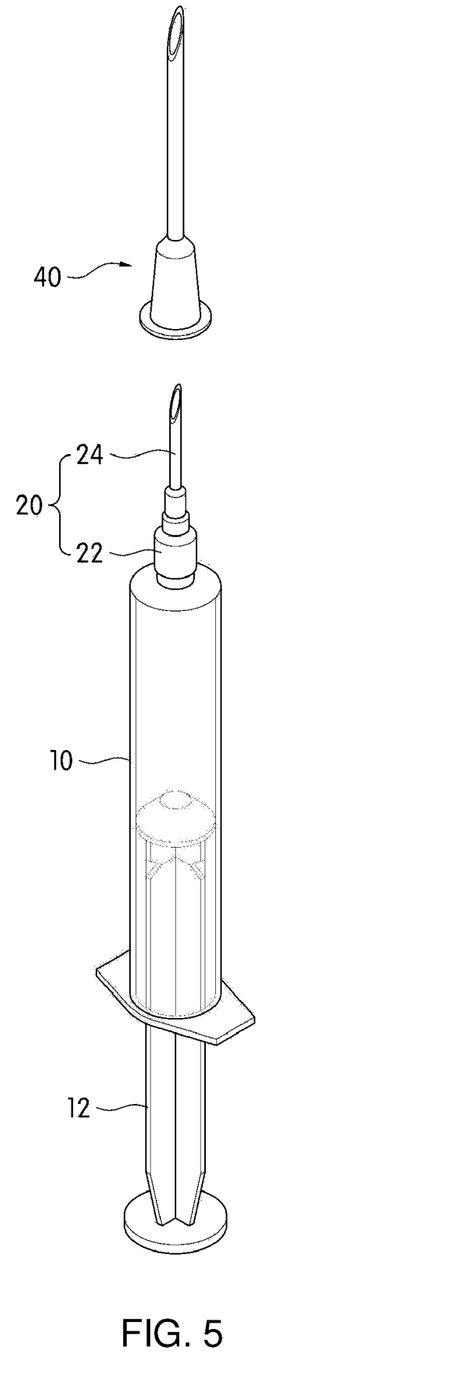
FIG. 5 is an exploded perspective view of an injection device to which a filter module according to an embodiment of the present invention is applied.
Figure 6:
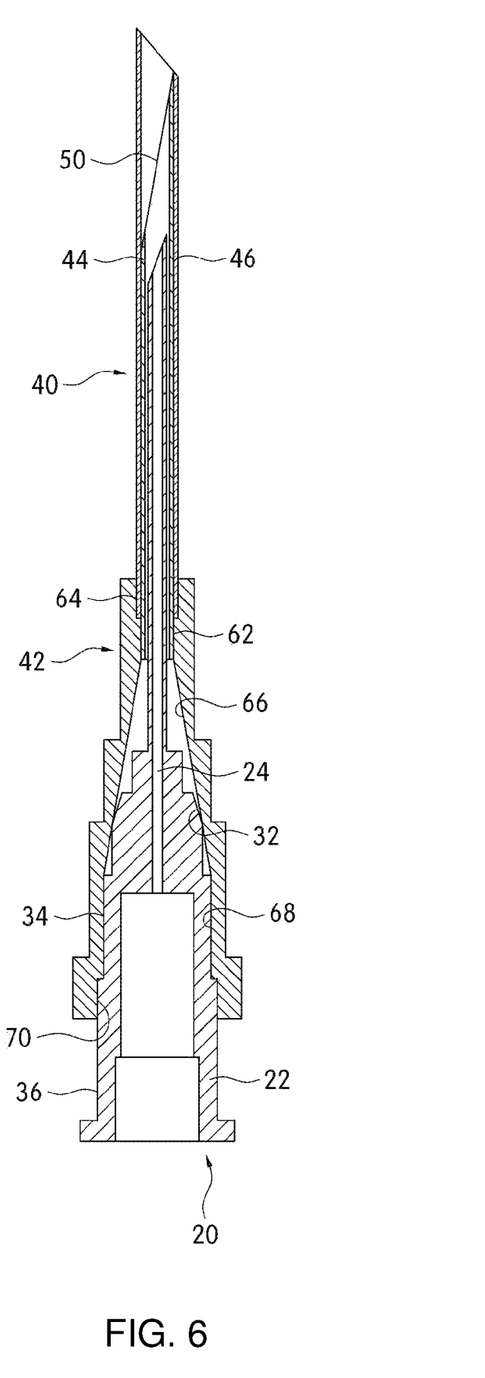
FIG. 6 is a cross-sectional view of a filter module according to one embodiment of the present invention.

The injection needle 20 includes a main body portion 22 sealably mounted on the cylinder 10 and a needle portion 24 integrally connected to the main body portion 22 and formed of a metal material. Further, the filter module 40 includes a hub 42 sealably mounted on the main body portion 22 of the injection needle 20, a tube 44 connected to the hub 42 and into which the needle portion 24 of the injection needle 20 is inserted, a metal barrel 46 connected to the hub 42 and into which the tube 44 is inserted to pass through a rubber stopper of a vial container; and a liquid drug-filtering filter medium 50 mounted in the tube 44 to filter foreign matter.

The hub 42 is formed of a resin material, and the tube 44 and metal barrel 46 may be connected to the hub 42 by a method such as heat fusion, bonding and the like, and the tube 44 and the metal barrel 46 may be formed integrally with the hub 42 by insert injection.

Figure 7:
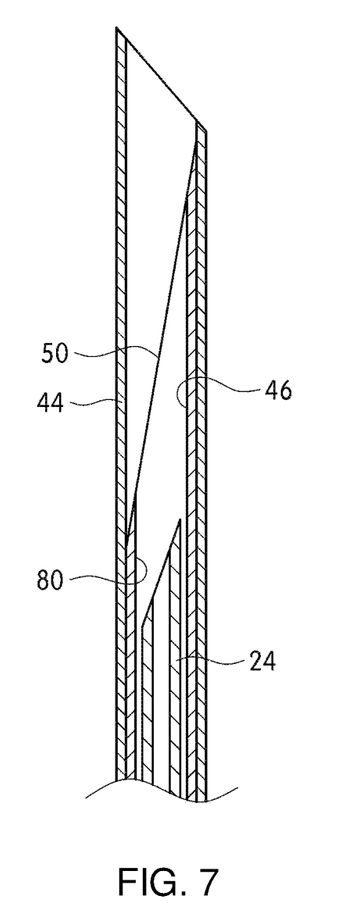
FIG. 7 is a partially enlarged cross-sectional view of a filter module according to one embodiment of the present invention.
Figure 8:
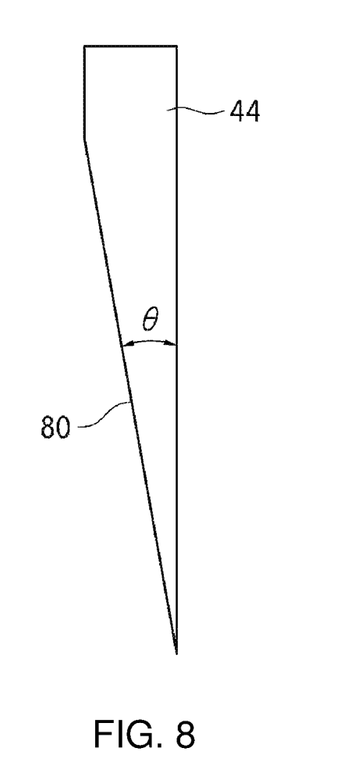
FIG. 8 is a lateral view of a tube provided in a filter module according to one embodiment of the present invention.

The tube 44 is formed of a resin material, and has an inner diameter larger than the outer diameter of the needle portion 24 so that the needle portion 24 of the injection needle 20 can be inserted into the tube 44, and a filter mounting portion 80 on which the filter medium 50 is mounted is formed at an end portion of the tube 44. Here, the filter mounting portion 80 may be formed as an inclined surface so as to increase an effective filtration area of the filter medium 50 provided in the filter module 40. That is, as shown in FIGS. 7 and 8, the filter mounting portion 80 is formed as an inclined surface at a predetermined angle to the end portion of the tube 44 and has an elliptical cross-section. When the filter medium 50 is mounted on the elliptical cross-section, the cross-sectional area of the filter medium 50 may be wide.

The inclination angle (θ) of the filter mounting portion 80 may be in the range of 10° to 45°, and preferably, the inclination angle (θ) of the filter mounting portion 80 may be in the range of 10° to 20°. When the inclination angle is less than 10°, an effective filtration area through the filter medium increases, but the nanofiber web of the filter medium 50 may be torn or damaged due to the pressure of the inflowing liquid drug. Further, when the inclination angle is more than 45°, it may be difficult to obtain the desired level of the flow amount.

The filter medium 50 may be mounted and fixed on the filter mounting portion 80, and for example, may be fixed by heat fusion. That is, when heat is applied to the edge of the filter medium 50 contacting the filter mounting portion 80, the support edges of the filter medium 50 and the filter mounting portion 80 may be molten by heat and bonded to each other.

The present invention will now be described more specifically with reference to the following examples, but the following examples should not be construed as limiting the scope of the present invention.

EXAMPLES

Example 1

First, in order to prepare a spinning solution, 9 parts by weight of polyacrylonitrile (PAN, Dolan Corp., N-PAN, a weight average molecular weight of 85,000) was mixed based on 100 parts by weight of polyvinylidene fluoride (Arkema, Kynar 761), as fiber forming components, and 12 g of the fiber forming components were dissolved in 88 g of dimethylacetamide at a temperature of 80° C. for 6 hours using a magnetic bar to prepare a mixed solution. Thereafter, the mixed solution was cooled to room temperature, and 3 parts by weight of a nonionic emulsifying agent (Daejung Chemical and Metals Co., Ltd, Tween 80, a hydrophile-lipophile balance of 15) was included based on 100 parts by weight of the fiber-forming ingredient to prepare a spinning solution. The spinning solution was added into a solution tank of the electrospinning device as shown in FIG. 4, and discharged at a rate of 15 µl/min/hole. Here, the temperature of the spinning section was maintained at 28° C., the humidity was maintained at 40%, the distance between the collector and the tip of the spinning nozzle was 18 cm, and the thickness of the support layer on the collector was 100 µm. After a non-woven fabric (Namyang Nonwoven Fabric Co., Ltd, CCP40) formed of a low-melting point composite fiber including a low-melting point polyethylene as a sheath part and polypropylene as a core part was disposed, a voltage of 40 kV was applied to a spin nozzle pack using a high voltage generator, and at the same time, air was emitted at an air pressure of 0.03 MPa to each nozzle of the spin pack in parallel to a discharge direction to prepare a fiber web formed on one surface of a nonwoven fabric and formed of PAN/PVDF nanofibers. Next, heat treatment was performed at a temperature of 160° C. to dry the solvent and moisture remaining in the fiber web, and a calendering process was performed twice at a temperature of 185° C. and a pressure of 1 kgf/cm² to prepare a filter medium for filtering a liquid drug.

Examples 2 to 16

Filter media for filtering a liquid drug as shown in the following Table 1, 2 or 3 were prepared in the same manner as in Example 1 except that the composition of the spinning solution was changed as shown in the following Table 1, 2 or 3.

Here, the types of modified emulsifying agents are shown in the following Table 4.

Experimental Example

The following physical properties of the filter media prepared in Examples 1 to 16 were evaluated and shown in the following Table 1, 2 or 3.

1. Diameter Uniformity of Fiber Web Nanofibers

The average diameter and standard deviation of the nanofibers forming the fiber web were measured through a program (manufactured by Amogreentech Co., Ltd.) which measures a fiber diameter using a contrast ratio of the image obtained after photographing the SEM image of a surface of the spun fiber web and the slope of the fiber. The diameter uniformity was calculated according to the following Mathematical Equation 1 using the measured average diameter and standard deviation.

[Mathematical Equation 1]

$$\text{Uniformity of nanofiber diameter (\%)} = \frac{\text{Standard deviation of nanofiber diameter (nm)}}{\text{Average diameter of nanofiber (nm)}} \times 100$$

2. Spinnability

SEM photographs were taken at a magnification of 2000× with respect to the surface of the spun fiber web, the total number of fibers and the number of beads were counted on the photographed image, and then spinnability was calculated according to the following Mathematical Equation 2.

[Mathematical Equation 2]

$$\text{Spinnability (\%)} = \frac{\text{Total number of fibers} - \text{number of beads}}{\text{Total number of fibers}} \times 100$$

3. Wettability of Fiber Web

In order to evaluate the miscibility of PVDF and PAN as the fiber-forming ingredients of the nanofiber, water was sprayed onto the upper portion of the surface of the fiber web of the filter medium having a width of 20 cm and a length of 20 cm. Then, the degree of wetting of the surface of the fiber web by the sprayed water was confirmed with the naked eye, the area of the wetted portion of the fiber web was measured, and the measured value was converted into a percentage based on the total area.

In the same content of PAN, the higher the miscibility, the larger the wetted area was. Further, when the hydrophilicity of the nanofiber is low such as a case in which the PVDF and the PAN are separated or the content of the PAN is low, an unwet area is formed.

TABLE 1

|  |  | Example 1 | Example 2 | Example 3 | Example 4 | Example 5 | Example 6 |
|---|---|---|---|---|---|---|---|
| Spinning solution | PVDF (parts by weight) | 100 | 100 | 100 | 100 | 100 | 100 |
|  | PAN (parts by weight) | 9 | 9 | 9 | 9 | 9 | 9 |
|  | Emulsifying agent (type/content[1]/HLB) | Nonionic/ 3/15 | Nonionic/ 0.3/15 | Nonionic/ 0.7/15 | Nonionic/ 8.5/15 | Cationic/ 3/10 | Anionic/ 3/40 |
| Filter medium | Spinnability (%) | 100 | 97.2 | 99.97 | 95.46 | 83.52 | 79.9 |
|  | Diameter uniformity of nanofibers (%) | 15.26 | 34.16 | 22.34 | 41.23 | 61.42 | 66.89 |
|  | Wettability (%) | 100 | 100 | 100 | 100 | 100 | 100 |

[1]The contents are based on 100 parts by weight of the fiber forming components, and the units are parts by weight.

TABLE 2

|  |  | Example 7 | Example 8 | Example 9 | Example 10 | Example 11 |
|---|---|---|---|---|---|---|
| Spinning solution | PVDF (parts by weight) | 100 | 100 | 100 | 100 | 100 |
|  | PAN (parts by weight) | 9 | 9 | 9 | 9 | 9 |
|  | Emulsifying agent (type/content[1]/HLB) | Amphoteric/ 3/13 | Nonionic/ 3/8.6 | Nonionic/ 3/11 | Nonionic/ 3/16.7 | Nonionic/ 3/19.1 |
| Filter medium | Spinnability (%) | 82.15 | 96.18 | 99.12 | 97.30 | 95.64 |
|  | Diameter uniformity of nanofibers (%) | 62.10 | 38.59 | 24.46 | 26.11 | 41.48 |
|  | Wettability (%) | 100 | 100 | 100 | 100 | 100 |

[1]The contents are based on 100 parts by weight of the fiber forming components, and the units are parts by weight.

TABLE 3

|  |  | Example 12 | Example 13 | Example 14 | Example 15 | Example 16 |
|---|---|---|---|---|---|---|
| Spinning solution | PVDF (parts by weight) | 100 | 100 | 100 | 100 | 100 |
|  | PAN (parts by weight) | 3 | 7 | 18 | 22 | 9 |
|  | Emulsifying agent (type/content[1)]/HLB) | Nonionic/ 3/15 | Nonionic/ 3/15 | Nonionic/ 3/15 | Nonionic/ 3/15 | 0 |
| Filter medium | Spinnability (%) | 100 | 100 | 100 | 98.56 | 75.61 |
|  | Diameter uniformity of nanofibers (%) | 17.59 | 19.37 | 28.4 | 30.22 | 44.81 |
|  | Wettability (%) | 0 | 12 | 100 | 100 | 15 |

[1)]The contents are based on 100 parts by weight of the fiber forming components, and the units are parts by weight.

It can be confirmed from Tables 1 to 3 that, in the case of Example 16 including no emulsifying agent, the miscibility of PVDF and PAN was poor, and thus wettability was remarkably lowered as compared to Example 1.

Further, it can be confirmed that, in the case of examples in which cationic (Example 5), anionic (Example 6), and amphoteric (Example 7) emulsifiers are contained, spinnability is notably lower than that of Example 1 in which a nonionic emulsifying agent is contained. Further, it can be confirmed that the nanofiber diameter uniformity was poor because spinning was performed so that a large amount of beads are contained in the nanofibers.

Further, it can be seen that, even in the case where the nonionic emulsifying agent is contained, there was a difference in the nanofiber diameter uniformity depending on an HLB value and contents, and in the case of Examples 1 and 3, in which the content of the emulsifying agent is within the preferable range of the present invention, the diameter uniformity is excellent as compared with Examples 2 and 4 in which the diameter uniformity is out of the preferable range.

Further, it can be confirmed that, the nanofiber diameter uniformity in Examples 1, 9 and 10 in which the HLB values of the nonionic emulsifier are within the preferred ranges of the present invention, is superior to that of Examples 8 and 11 in which the HLB values of the nonionic emulsifier are out of the range.

Further, it may be confirmed that the wettability of Examples 12 and 13, in which the content of PAN is less than 8 parts by weight, is poor as compared with Example 1. On the other hand, in the case of Example 15 in which the content of PAN is more than 20 parts by weight, there was no problem in the evaluation results of nanofiber diameter uniformity and wettability as compared with Example 1, but the average diameter of a nanofiber is 300 nm in the case of Example 15 which is thicker than the average nanofiber diameter of 214 nm in the case of Example 1, and thus it is disadvantageous for implementing a fiber web with a smaller pore size.

TABLE 4

|  | Types | Product name | HLB |
|---|---|---|---|
| Example 5 | Cationic | CTAB | 10 |
| Example 6 | Anionic | SLS | 40 |
| Example 7 | Amphoteric | Tego | 13 |
| Example 8 | Nonionic | Sorbitan laurate | 8.6 |
| Example 9 | Nonionic | Poly sorbate 85 | 11 |
| Example 10 | Nonionic | Tween 20 | 16.7 |
| Example 11 | Nonionic | PEG 80 sorbitan laurate | 19.1 |

Example 17

First, in order to prepare a spinning solution, 12 g of polyvinylidene fluoride (Arkema, Kynar 761) as a fiber forming component was dissolved in 88 g of a mixed solvent prepared by mixing dimethylacetamide and acetone in a weight ratio of 70:30 at a temperature of 80° for 6 hours using a magnetic bar to prepare a mixed solution. Thereafter, the spinning solution was added into a solution tank of the electrospinning device as shown in FIG. 4, and discharged at a rate of 15 µl/min/hole. Here, the temperature of the spinning section was maintained at 30° C., the humidity was maintained at 50%, and the distance between the collector and the tip of the spinning nozzle was 20 cm. A non-woven fabric (Namyang Nonwoven Fabric Co., Ltd, CCP40) having a thickness of about 100 µm and a melting point of about 120° C. and formed of a low-melting point composite fiber including polyethylene as a sheath part and polypropylene as a core part was disposed on top of the collector, and then a voltage of 40 kV was applied to a spin nozzle pack using a high voltage generator, and at the same time, air was emitted at an air pressure of 0.03 MPa to each nozzle of the spin pack in parallel to a discharge direction to prepare a laminate in which a nanofiber web formed of PVDF nanofibers is formed on one surface of the support. Next, heat at a temperature of 140° C. and a pressure of 1 kgf/cm$^2$ were applied to perform a calendering process to dry the solvent and moisture remaining in the fiber web and to thermally fuse the support and the nanofiber web.

The laminate thus prepared was immersed in the hydrophilic coating layer-forming composition prepared in the following preparation example, and then dried in a dryer at a temperature of 110° C. for 5 minutes to prepare a filter medium for filtering a liquid drug as shown in the following Table 5 in which a hydrophilic coating layer was formed on the surface of the nanofibers of the nanofiber web.

Preparation Example: Hydrophilic Coating Layer-Forming Composition 7142 parts by weight of ultrapure water was mixed with 100 parts by weight of polyvinyl alcohol (Kuraray Co., PVA217) as a hydrophilic component, and PVA was dissolved therein using a magnetic bar at a temperature of 80° for 6 hours to prepare a mixed solution. Thereafter, the mixed solution was cooled to room temperature, and polyacrylic acid-co-maleic acid (Sigma-Aldrich Co. Llc, PAM) as a crosslinking agent was mixed with the mixed solution so that the polyacrylic acid-co-maleic acid was included at 15 parts by weight based on 100 parts by weight of polyvinyl alcohol, and dissolved at room temperature for 12 hours. Then, isopropyl alcohol (Duksan Chemical Co., IPA) was added to the mixed solution so that isopropyl alcohol was included at 7142 parts by weight based on 100 parts by weight of the polyvinyl alcohol, and a mixture was mixed for 2 hours to prepare a hydrophilic coating layer-forming composition.

Examples 18 to 21

Liquid drug-filtering filter media as shown in Table 5 were prepared in the same manner as in Example 17 except that the content of isopropyl alcohol in the hydrophilic coating layer-forming composition was changed as shown in the following Table 5.

Experimental Example 2

The wettability of the nanofiber web of the filter media prepared in Examples 17 to 21 was evaluated. Specifically, the contact angle between the membrane surface and the water droplet surface was measured with a contact angle (°) measuring device to measure the wettability of the surface of the nanofiber web with respect to water. A method of capturing the shape of a droplet using a CCD camera and calculating an interfacial tension (γ) optimized for the shape of the finally captured droplet was used. The injection volume was set as 0.05 mL through a microsyringe, and secondary distilled water was used. Since a contact angle error may occur according to the chemical non-uniformity and coarseness of the surface of the nanofiber web, the experiment was performed by 10 times or more of analysis so that an error does not exceed maximum ±2°. When the result of Example 21 was set as 100%, the wetting angles of Examples 17 to 20 were calculated in relative proportions and shown in Table 5.

TABLE 5

|  |  | Example 17 | Example 18 | Example 19 | Example 20 | Example 21 |
| --- | --- | --- | --- | --- | --- | --- |
| Hydrophilic coating layer-forming composition | PVA (parts by weight) | 100 | 100 | 100 | 100 | 100 |
|  | Isopropyl alcohol (parts by weight) | 7142 | 1050 | 950 | 500 | 0 |
| Filter medium | Wetting angle (%) | 20 | 27 | 44 | 55 | 100 |

It can be confirmed from Table 5 that, the degree of hydrophilization varied depending on the content of isopropyl alcohol as a wettability enhancer provided in the composition even when hydrophilic coating was performed, and in the case of Examples 17 and 18 in which the wettability enhancer is contained in an amount of 1000 parts by weight or more based on 100 parts by weight of the PVA, which is the preferred content range of the wettability enhancer of the present invention, the degree of improvement of the wetting angle is superior to those of Examples 19 to 21.

Example 22

A liquid drug-filtering filter medium was prepared in the same manner as in Example 1 except that a nanofiber web was prepared by spinning nanofibers by supplying air at an air pressure of 0.22 MPa in the electrospinning process of nanofibers.

Experimental Example 3

The nanofiber diameter uniformity of the nanofiber web of the filter media prepared in Examples 1 and 22 was evaluated and shown in Table 6. Specifically, the average diameter and standard deviation of the nanofibers forming the fiber web were measured through a program (manufactured by Amogreentech Co., Ltd.) which measures a fiber diameter using a contrast ratio of the image obtained after photographing the SEM image of a surface of the spun fiber web and the slope of the fiber. The diameter uniformity was calculated according to the above Mathematical Equation 1 using the measured average diameter and standard deviation.

TABLE 6

|  |  | Example 1 | Example 22 |
| --- | --- | --- | --- |
| Nanofiber web | Air pressure during spinning (MPa) | 0.03 | 0.22 |
|  | Nanofiber diameter uniformity (%) | 15.26 | 39.9 |

As can be seen from Table 6, in the case of Example 22 in which air was emitted at a stronger intensity in comparison with the case of Example 1 in which air was emitted at a pressure of 0.03 MPa in parallel with the discharge direction of the spinning solution during electrospinning, the nanofiber diameter uniformity was reduced, and thus it can be expected that the filtration efficiency, durability and the like are lower than those in Example 1.

Although certain embodiments of the present embodiment have been described, it shall be appreciated that the technical ideas of the present invention are not restricted to the described embodiments and that other embodiments are possible within the same or equivalent technical ideas by those skilled in the art to which the present invention pertains by adding, modifying, deleting and supplementing the elements.

The invention claimed is:

1. A liquid drug-filtering filter medium, comprising a nanofiber web having a three-dimensional network structure for filtering foreign matter included in a liquid drug, wherein the nanofiber web includes a nanofiber including fiber-forming components including polyacrylonitrile (PAN) and polyvinylidene fluoride (PVDF) and an emulsifying agent for improving the miscibility of the fiber-forming components, and the fiber-forming components include polyacrylonitrile at 8 to 20 parts by weight based on 100 parts by weight of polyvinylidene fluoride, and the nanofiber includes an emulsifying agent at 0.5 to 8 parts by weight based on 100 parts by weight of the fiber-forming components.

2. The liquid drug-filtering filter medium according to claim 1, wherein the nanofiber web is formed of a nanofiber having an average diameter of 0.1 to 3 μm.

3. The liquid drug-filtering filter medium according to claim 1, wherein the nanofiber web has a porosity of 40 to 90%, and an average pore diameter of 0.3 to 10 μm.

4. The liquid drug-filtering filter medium according to claim 1, wherein the nanofiber web has a basis weight of 1 to 10 g/m².

5. The liquid drug-filtering filter medium according to claim 1, wherein the nanofiber web has a thickness of 1 to 20 μm.

6. The liquid drug-filtering filter medium according to claim 1, wherein the filter medium further includes a support disposed at one or both surfaces of the nanofiber web.

7. The liquid drug-filtering filter medium according to claim 6, wherein the support is one or more of a woven fabric, a knitted fabric or a nonwoven fabric.

8. The liquid drug-filtering filter medium according to claim 6, wherein, the support includes:

a first support; and a second support disposed to surround side surfaces of the first support and having a melting point lower than that of a first support component forming the first support.

9. The liquid drug-filtering filter medium according to claim 8, wherein the first support component has a melting point of 180° C. or more, and the second support component has a melting point of 100 to 140° C.

10. The liquid drug-filtering filter medium according to claim 2, wherein the nanofiber has a nanofiber diameter uniformity of 25% or less according to the following Mathematical Equation 1:

$$\text{Uniformity of nanofiber diameter (\%)} = \frac{\text{Standard deviation of nanofiber diameter (nm)}}{\text{Average diameter of nanofiber (nm)}} \times 100.$$ [Mathematical Equation 1]

11. The liquid drug-filtering filter medium according to claim 1, wherein the emulsifying agent is a nonionic emulsifying agent which improves spinnability, and the nonionic emulsifying agent satisfies a hydrophile-lipophile balance (HLB) of 10 to 18.

12. A liquid drug-filtering filter module, comprising:

the liquid drug-filtering filter medium according to claim 1; and a housing, including a liquid drug-inlet portion and a discharge portion through which a filtered liquid drug is discharged, and having the filter medium inside thereof.

13. An injection device, comprising:

the liquid drug-filtering filter module according to claim 12; and an injection module connected to a discharge portion of the liquid drug-filtering filter module.

* * * * *